(12) United States Patent
Lehmbeck (10) Patent No.: US 6,291,209 B1
(45) Date of Patent: Sep. 18, 2001

(54) ALKALINE PROTEASE DEFICIENT FILAMENTAOUS FUNGI

(75) Inventor: Jan Lehmbeck, Veksø(DK)

(73) Assignee: Novo Nordisk A/S Novo allé, Bagsvaerd (DK)

( * ) Notice: Subject to any disclaimer, the term of this patent is extended or adjusted under 35 U.S.C. 154(b) by 0 days.

(21) Appl. No.: 09/148,751

(22) Filed: Sep. 4, 1998

Related U.S. Application Data (63) Continuation of application No. PCT/DK97/00135, filed on Mar. 26, 1997.

(30) Foreign Application Priority Data

Mar. 27, 1996 (DK) .................................................. 0354/96
May 9, 1996 (DK) .................................................. 0555/96

(51) Int. Cl.$^7$ .................................................. C12N 15/64
(52) U.S. Cl. .................... 435/69.1; 435/484; 435/254.3; 435/320.1
(58) Field of Search .............................. 435/6, 69.1, 183, 435/194, 320.1, 254.21, 254.3, 256.1, 477, 484

(56) References Cited

FOREIGN PATENT DOCUMENTS

| 0 414 297 A1 | 2/1981 | (EP) . |
| 0 574 347 A2 | 12/1993 | (EP) . |
| WO 90/00192 | 1/1990 | (WO) . |
| WO 92/17595 | 10/1992 | (WO) . |

OTHER PUBLICATIONS

Murakami et al., Agric. Biol. Chem., vol. 55, 1991, pp. 2807–2811.*
Dialog Information Service, File 155, Medline, Accession No. 7701294.
Dialog Information Service, File 5, Biosis, Accession No. 11494130.
Dialog Information Service, File 155, Medline, Accession No. 07408772.
Tang et al., "An *Aspergillus Fumigatus* Alkaline Protease Mutant Constructed By Gene Disruption Is Deficient In Edtracellular Elastase Activity", Molecular Mocrobiology (1992) 6 (12), pp. 1663–1671.
Tatsumi et al., "A Full Length cDNA Clone For The Alkaline Protease From *Asperfillus Oryzaie* : Structural Analysis And Expression in *Saccharomyces Cerevisiae* ", Mol. Gen. Genet (1989) 219, pp. 33–38.

* cited by examiner

*Primary Examiner*—James Ketter
(74) *Attorney, Agent, or Firm*—Jason I. Gorbell (57) ABSTRACT

The present invention relates to a filamentous fungus useful for the production of heterologous polypeptides, having been modified by recombinant DNA technology in a manner by which the expression of alkaline proteases have been completely or partially inactivated. The invention also encompasses processes for the production of proteins of interest in high yields by using the fungi of the invention. The invention furthermore relates to methods for producing such fungi and DNA constructs to be used in these methods.

27 Claims, 5 Drawing Sheets

A. oryzae IFO 4177

Transformation with the 2.2 kb Hind III fragment of pSO5 harboring the 5' and the 3' flanking sequence of the A. oryzae pyrG gene.

A. oryzae HowB 101 (pyrG mutant)

Transformation with the the 6.8 kb SacI–SphI fragment of pJaL212 harboring the 5' and 3' flanking sequences of the alp gene separated by the pyrG gene, and selection for uridine auxotrophs.

A. oryzae JaL125 (alp deleted)

ND OF THE INVENTION

The present invention relates to novel fungal host cells and to methods of producing proteins. More specifically, the invention relates to a host cell useful for the expression of heterologous proteins, in which the host cell has been genetically modified in order to express significantly reduced levels of alkaline protease activity. Moreover, the invention relates to a method of producing proteins of interest in high yields by using the fungi of the invention, in which the method comprises cultivating the host cell in a suitable growth medium, followed by recovery of the desired protein. The invention also comprises methods for producing such fungi and DNA constructs to be used in these methods.

BACKGROUND OF THE INVENTION

Fungi, and especially filamentous fungi, are widely used commercially as host cells for the expression of proteins which are secreted extracellularly. In particular, species belonging to the genus Aspergillus have a long history of commercial use for the production of endogenous and lately also heterologous proteins.

One disadvantage frequently encountered with microorganisms used as host cells is the inherent production and secretion of high levels of proteolytic enzymes which may result in reduced yields of a protein product of interest due to proteolysis.

Various solutions to circumvent this have been envisaged. For example, one could delete or disrupt the genes encoding the various endogenous proteases. WO 90/00192 (Genencor Inc.) describes mutant filamentous fungal hosts which have been rendered incapable of secreting enzymatically active aspartic protease. By such mutation, it was shown that the yield of the heterologous polypeptide, bovine chymosin, was increased. EP 574 347 (Ciba Geigy AG) describes an Aspergillus host defective in a serine protease of the subtilisin type.

However, it is well known that fungi produce a large number of proteases in addition to the two herein mentioned. Consequently, strains of filamentous fungi exhibiting no or very low levels of proteolytic activity originating from other proteases are still needed.

SUMMARY OF THE INVENTION

It is an objective of the present invention to provide filamentous fungal host cells for the production of heterologous polypeptide products in which the cell has been genetically modified in order to express significantly reduced levels of an endogenous alkaline protease, by comparison to the parental cell.

The present invention relates to such modified fungi, wherein transcription and/or translation of at least one gene encoding an alkaline protease activity has been completely or partially inhibited.

According to the invention, this may be accomplished through the use of recombinant DNA technology wherein gene sequences encoding alkaline protease activity of the fungus in question is deleted or mutated, resulting in reduced levels of protease expression or expression of a protease with reduced levels of activity.

In a specific embodiment the alkaline protease gene is the alp gene shown in SEQ ID No 1 and described by Murakami, K., et al., 1991, Agric. Biol. Chem. 55:2807–2811.

Furthermore, the invention relates to methods for producing such fungi, wherein the inactivation of the alkaline gene(s) is(are) obtained by nucleotide substitution, deletion or insertion in the alkaline protease gene.

The invention also relates to processes for producing heterologous polypeptides using fungal host cells of the invention. Especially contemplated are secreted polypeptides, wherein a fungal host cell, modified and optionally transformed with a DNA construct comprising at least a DNA sequence encoding the polypeptide or gene product of interest, is cultivated in a suitable growth medium under appropriate conditions and the desired gene product is recovered and purified.

By the methods described herein, it has been found that the yield of polypeptides secreted by fungi of the invention is much improved.

Furthermore, the invention relates to polypeptide products produced by the above methods.

Lastly, the invention relates to DNA constructs comprising the DNA sequence of the alp gene of *Aspergillus oryzae* intended for use in the above mentioned methods.

BRIEF DESCRIPTION OF THE FIGURES

The invention is described in further detail in the specification with reference to the Examples and the following figures, wherein.

DEFINITIONS

In the present specification the following definitions are used:

alpD means a strain in which the alp gene is deleted.

alp⁻ means a strain which does not produce a functional Alp polypeptide i.e., an Alp protein without proteolytic activity.

The term "functional analogue" as used in relation to the alp sequence shown in SEQ ID NO 1 is intended to indicate a DNA sequence encoding an alkaline protease which hybridises to the DNA sequence shown in SEQ ID NO 1 under certain specified conditions which are described in detail below and which exhibits a degree of homology of at least 70%.

Suitable conditions for determining hybridisation between a nucleotide probe and a homologous DNA or RNA sequence involves presoaking of the filter containing the DNA fragments or RNA to hybridise in 5×SSC (standard saline citrate) for 10 min, and prehybridisation of the filter in a solution of 5'SSC (Sambrook et al. 1989), 5×Denhardt's solution (Sambrook et al., ibid), 0.5% SDS and 100 µg/ml of denatured sonicated salmon sperm DNA (Sambrook et al., ibid), followed by hybridisation in the same solution containing a random-primed, $^{32}$P-dCTP-labeled (specific activity>1×10$^9$ cpm/µg) probe for 12 hours at ca. 45° C. (Feinberg, A. P., and Vogelstein, B. 1983 Anal. Biochem. 132:6–13). The filter is then washed two times for 30 minutes in 2×SSC, 0.5% SDS at preferably not higher than 50° C., more preferably not higher than 55° C., more preferably not higher than 60° C., more preferably not higher than 65° C., even more preferably not higher than 70° C., especially not higher than 75° C.

Molecules to which the oligonucleotide probe hybridizes under these conditions are detected using a x-ray film.

The DNA sequence homology referred to above is determined as the degree of identity between the two sequences indicating a derivation of the first sequence from the second. The homology may be suitably determined by means of computer programs known in the art, such as GAP provided in the GCG program package (Needleman, S. B., and Wunsch, C. D. 1970, Journal of Molecular Biology 48:443–453). Using GAP with the following settings for DNA sequence comparison: GAP creation penalty of 5.0 and GAP extension penalty of 0.3, the coding region of the DNA sequence exhibits a degree of identity preferably of at least 70%, more preferably at least 80%, more preferably at least 90%, more preferably at least 95%, more preferably at least 97% with the enzymX encoding part of the DNA sequence shown in SEQ ID NO 1.

DETAILED DESCRIPTION OF THE INVENTION

The present invention relates, in its first aspect, to fungi useful for the production of heterologous peptides which have been modified by recombinant DNA technology such that one or more endogenous alkaline protease activities have been completely or partially inactivated.
Genetic Modifications The fungi of the invention may be modified using standard techniques of recombinant DNA technology known to the person skilled in the art. The gene sequence responsible for the production of alkaline proteases may be partially inactivated or eliminated entirely.

In other words, a fungus of the invention expresses alkaline protease activity at reduced levels, or expresses no alkaline protease activity at all, or expresses (an) enzymatically inactive alkaline protease(s). In one aspect of the invention, such inactivation or reduced levels of alkaline protease activity may be achieved by nucleotide deletion, insertion or substitution in a sequence encoding an alkaline protease gene product.

In a particular embodiment, said inactivation is obtained by modification in the structural or regulatory sequence encoding the alkaline protease(s) in question, for instance, by interfering with the regulation of the expression signals regulating the expression of the alkaline protease gene.

Known and useful techniques include, but are not limited to, specific or random mutagenesis, PCR generated mutagenesis, site specific DNA deletion, insertion and/or substitution, gene disruption or gene replacement techniques, anti-sense techniques, or any combination thereof.

Mutagenesis may be performed using a suitable physical or chemical mutagenizing agent. Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulfite, formic acid, and nucleotide analogues. When such agents are used, the mutagenesis is typically performed by incubating the cell to be mutagenized in the presence of the mutagenizing agent of choice under suitable conditions for the mutagenesis to take place, and selecting for mutated cells producing significantly reduced levels of alkaline protease(s).

Modification resulting in inactivation or reduced alkaline protease activity may also be accomplished by the introduction, substitution or removal of one or more nucleotides in the alkaline protease encoding sequence or a regulatory element required for the transcription or translation thereof. Nucleotides may, e.g., be inserted or deleted so as to result in the introduction of a stop codon, the removal of a start codon or a change of the open reading frame. The modification or inactivation of the structural sequence or a regulatory element may be accomplished by site-directed mutagenesis or PCR generated mutagenesis in accordance with methods known in the art. Although in principle the modification may be performed in vivo, i.e., directly on the cell carrying the alkaline protease gene, it is presently preferred that the modification is conducted in vitro.

A convenient method to inactivate or reduce the alkaline protease production of a fungal host cell of choice is based on the principles of gene interruption. This method involves the use of a DNA sequence encoding the endogenous gene or gene fragment targeted to be mutated. Said DNA sequence is mutated in vitro resulting in a defective gene which is then transformed into the fungus. By homologous recombination, the defective gene replaces the endogenous gene or gene fragment. It may be desirable to include a genetic marker to be used for the selection of transformants of interest.

Methods for gene deletion or disruption are specifically described in Miller et al., 1985, Mol. Cell. Biol. 5:1714–1721; WO 90/00192 (Genencor); May G., 1992, Applied Molecular Genetics of Filamentous Fungi pp. 1–25, J. R. Kinghorn and G. Turner, Eds., Blackie Academic and Professional; and, in G. Turner, 1994, Vectors for genetic manipulation, pp. 641–665, S. D. Martinelli and J. R. Kinghorn, Eds., Elsevier.

Alternatively, the modification and/or inactivation of the DNA sequence may be performed by use of established anti-sense techniques using a nucleotide sequence complementary to the alkaline protease encoding sequence, e.g. the alp gene nucleotide sequences presented as SEQ ID NO. 1 or a functional analogue thereof.

Anti-sense technology and its employ are described in detail in U.S. Pat. No. 5,190,931 (University of New York).

As a result of the aforementioned genetic modification, the fungi of the invention express significantly reduced levels of alkaline protease activity. In a preferred embodiment the level of alkaline protease activity is reduced more than about 50%, preferably more than about 85%, more preferably, more than about 90%, most preferably more than about 95%. In a most preferred embodiment, the host cell is essentially free of detectable alkaline protease activity.

The fungi of the invention may have the alkaline protease gene replaced with a selection marker, such as the pyrG gene, argB gene, sC gene, or the hph gene.

In a specific embodiment of the invention the alkaline protease gene comprises the alp gene sequence shown in SEQ ID NO 1 or a functional analogue thereof.

Alp is a serine protease with maximal enzymatic activity in the neutral to alkaline pH range. As deduced from the nucleotide sequence the mature Alp protein is a subtilisin-type serine protease consisting of 282 amino acids and a prepro region of 121 amino acids in the vicinity of the N-terminal. Comparison of the amino acid sequence between Alp and other subtilisin-type serine proteases suggest that three residues in Alp (Asp41, His72 and Ser228) form the catalytic site. That Ser228 is part of the catalytic site is supported by the loss of proteolytic activity observed when Ser228 is substituted with an alanine residue (Tatsumi et al., 1991, Agri. Biol. Chem. 55:3099–3101).

The Host Fungi

According to the invention the fungus preferably belongs to a genus selected from the group comprising Aspergillus, Trichoderma, Humicola, Candida, Acremonium, Fusarium, and Penicillium.

Among these genera, species selected from the group comprising *A. oryzae, A. niger, A. awamori, A. phoenicis, A. japonicus, A. foetidus, A. nidulans, T. reesei, T. harzianum, H. insulens, H. lanuginosa, F. graminearum, F. solani, F. venenatum,* and *P. chrysogenum* are preferred. For each of these species, the homologous alkaline protease gene may be inactivated or otherwise modified as explained herein.

Normally the fungus of the invention is transformed to render the fungus capable of producing the desired protein product.

Methods for transforming fungi are well known in the art, cf. e.g. EP 0 184 438 A2 (Gist-Brocades N.V.) and EP application No. 87103806 (Novo Nordisk A/S).

When the gene products of interest are indigenous to the host cell, transformation is not necessary, but to increase production it may be advantageous to incorporate multiple copies of the gene encoding the protein of interest into the fungi of the invention.

Method for Producing the Host Fungus

Another aspect of the invention comprises a method for producing the fungus of the first aspect of the invention, wherein said inactivation of the alkaline protease gene is obtained by the following steps:
  i) cloning homologues of the alkaline protease gene from a fungal host cell,
  ii) producing a DNA construct comprising the alkaline protease gene wherein a part of an internal sequence has been modified by nucleotide substitution, deletion, or insertion,
  iii) transforming said fungus with the construct, and
  iv) selecting transformants which exhibit:
    1) no detectable alkaline protease activity,
    2) a reduced level of alkaline protease activity, or
    3) enzymatically inactive alkaline protease(s).

The term "reduced" alkaline protease activity means that the level of activity is less than the level exhibited by a non-mutated corresponding fungus.

The alkaline protease activity, including Alp activity, can be assayed with the synthetic substrate, N-succinyl-Ala-Ala-Pro-Phe-p-nitroanilide (Sigma Chemical Co.). The activity is measured at 25° C. with 1 mM substrate in 20 mM Tris-HCl pH 8.0 in a reaction volume of 1 ml. The release of p-nitroanilin is monitored at 410 nm (Ramesh et al., 1994, Infection and Immunity, Jan. 79–85).

Homologues of the alkaline protease gene in question in the aforementioned step i) may be cloned either by cross-hybridization with a previously identified gene for alkaline protease or by complementation of alkaline protease mutants.

The absence of measurable alkaline protease activity may result from a deletion in a sequence essential to synthesis of an alkaline protease gene product.

A reduced level of alkaline protease activity may result from an incomplete inactivation of all alkaline protease genes or to the expression of alkaline protease gene products with reduced functionality.

In connection with the aforementioned cloning, DNA constructs can be constructed to be integrated into the alkaline protease gene, or alternatively, the alkaline protease gene may be deleted and substituted with another gene, such as the pyrG gene, argB gene, sC gene, or the hph gene.

If the gene is the alp gene the isolated transformants may be alp$^-$ or alpD.

Another aspect of the invention relates to the method for producing the fungi, wherein the inactivation is obtained by using anti-sense technology, such method comprising the following steps:
  i) construction of an expression plasmid resulting in the synthesis of an RNA molecule complementary to the mRNA transcribed from the alkaline protease gene,
  ii) transformation of the host fungal cell with said expression plasmid and a suitable marker, either on separate plasmids or on the same plasmid,
  iii) selection of transformants using said marker, and
  iv) screening transformants for a reduction in the synthesis of the alkaline protease gene product.

A further aspect of the invention comprises DNA constructs for use in the above mentioned methods.

In respect of the methods relating to DNA constructs of the invention, said DNA constructs may comprise the alkaline protease gene, such as the alp gene, wherein a part of an internal sequence has been modified by nucleotide substitution, deletion, or insertion.

The DNA construct may furthermore also comprise DNA sequences encoding a polypeptide product of interest, such as those mentioned hereinafter.

In respect of the aforementioned anti-sense methods the DNA construct may comprise an inverted DNA sequence of an alkaline protease gene connected to a functional promoter, wherein the mRNA is at least partially complementary to an mRNA produced from an alkaline protease gene.

The Process

A further aspect of the invention relates to a process for the production of heterologous polypeptides, preferably a secreted gene product, wherein a fungus of the invention is cultivated in a suitable growth medium at appropriate conditions from which the desired gene product is recovered and purified.

When producing heterologous polypeptides, e.g., enzymes, the choice of fermentation pH will often depend on factors such as the host cell to be used, the growth medium required by the host cell, and the stability of the polypeptide. Consequently, although the fungi of the invention may be used for any fermentation process carried out at any pH, it is advantageous that the fermentation process is carried out at a pH at which the activites of endogenous acidic and/or neutral proteases produced by the host cell are rendered inactive or at least significantly reduced. Thus, if the fermentation process is carried out at, e.g., pH 5 to 11, such as 6 to 10.5, 7 to 10, or 8 to 9.5 the level of activity of acidic proteases (such as aspartic and serine proteases), as well as neutral proteases in the pH range above 7, will be reduced and may even be inactive. Hence, removal of aspartic proteases, such as described in WO 90/00192, will have only a limited effect on the production yield.

However, in the alkaline pH range, alkaline proteases in an unmodified host cell may be active and may be the main reason for degradation of the polypeptide product of interest.

Consequently, in such cases the inactivation of gene(s) encoding alkaline protease activity is especially advantageous.

Inactivation of alkaline protease gene(s) of the invention is also especially advantageous for certain hosts, as the acidic, neutral and alkaline protease activity varies among the various species of fungi. For instance, the alkaline protease activity in *Aspergillus oryzae* is higher than in *Aspergillus niger*.

Examples of enzymes that can be produced under fermention conditions in the above described alkaline pH range include endoglucanases, phytases, proteases, lipases, cutinases, cellulases, chymosins, peroxidases and protein disulfide isomerases.

The desired heterologous polypeptide may be recovered from the medium by conventional procedures, including separating the cells from the medium by centrifugation or filtration, if necessary after disruption of the cells, precipitating the proteinaceous components of the supernatant or filtrate by means of a salts, e.g., ammonium sulphate, followed by purification by any of a variety of chromatographic procedurs, e.g., ion exchange chromatography, affinity chromatography, and the like.

The Heterologous Polypeptide

In the context of the present invention, the desired polypeptide is a "heterologous polypeptide" which means a polypeptide which is not native to the fungal host cell of the invention, or is a native polypeptide in which modifications have been made to alter the native sequence (i.e., genetic variants), or is a native polypeptide whose expression is quantitatively altered as a result of a manipulation of a native regulatory sequence required for the expression of the native polypeptide, such as a promoter, a ribosome binding site, etc., or as a result of any other manipulation of the fungi of the invention by recombinant DNA techniques.

The heterologous polypeptide expressed by the fungus of the invention may also be a precursor protein, i.e. a zymogen, a hybrid protein, a protein obtained as a prosequence or pre-pro sequence, or in an otherwise immature form.

In another preferred embodiment, the product is an enzyme; in particular, a glycosidase enzyme, e.g., an amylase, in particular, an a-amylase or a b-amylase; a cellulase, in particular, an endo-1,4-b-glucanase (EC 3.2.1.4) or an endo-1,3-b-glucanase (3.2.1.6); a xylanase, in particular, an endo-1,4-b-xylanase (EC 3.2.1.8) or a xylan-endo-1,3-b-xylosidase (EC 3.2.1.32); an a-galactosidase (EC 3.2.1.22); a polygalacturonase (EC 3.2.1.15); a cellulose 1,4-b-cellobiosidase (EC 3.2.1.91); and an endoglucanase, in particular, an endo-1,6-b-glucanase (EC 3.2.1.75), an endo-1,2-b-glucanase (EC 3.2.1.71), an endo-1,3-b-glucanase (EC 3.2.1.39) or an endo-1,3-a-glucanase (EC 3.2.1.59).

In a preferred embodiment, the product is a eukaryotic polypeptide, such as insulin, growth hormone, glucagon, somatostatin, interferon, PDGF, factor VII, factor VIII, urokinase, erythropoetin, chymosin, tissue plasminogen activator, serum albumin, or thrombopoetin.

In another preferred embodiment, the product is a protein of fungal origin. In a preferred embodiment, the product is a fungal enzyme, e.g. an amylolytic enzyme, such as an a-amylase, a b-amylase, a glucoamylase, a b-galactosidase, a phytase, a cellulytic enzyme, a lipolytic enzyme, a xylanolytic enzyme, a proteolytic enzyme, an oxidoreductase, such as a peroxidase or a laccase, a pectinase, a cutinase, and a protein disulfide isomerase.

In yet another preferred embodiment, the product is a bacterial protein. In another preferred embodiment, the product is a bacterial enzyme; in particular, an amylolytic enzyme, e.g, an a-amylase or a b-amylase; a glucoamylase; a b-galactosidase; a cellulytic enzyme; a lipolytic enzyme; and a proteolytic enzyme.

Preferred hybrid polypeptides are prochymosin and protrypsin-like proteases.

The invention is explained in further detail in the Examples given below. These should, however, not in any way be construed as limiting the scope of the invention as defined in the appended claims.

EXAMPLES

Materials and Methods

Strains

| | |
|---|---|
| *Aspergillus oryzae* IFO 4177: | available from Institute for Fermentation, Osaka; 17–25 Juso Hammachi 2-Chome Yodogawa_ku, Osaka, Japan. |
| JaL125: | The construction of this strain is described in the Examples. |

Genes

| | |
|---|---|
| alp: | This gene codes for alkaline protease shown in SEQ ID NO 1. |
| pyrG: | This gene codes for orotidine-5'-phosphate decaroxylase, an enzyme involved in the biosynthesis of uridine. |

Plasmids pSO2: Prepared according to Example 1.

pSO5: Prepared from pSO2 according to Example 1.

pSRe403: Prepared according to Example 1.

pSX320: The construction of this plasmid is described in EP application No. 0 531 372B1.

pToC90: A subclone of p3SR2, harboring the amdS gene from *Aspergillus nidulans* as a 2.7 kb XbaI fragment (Corrick et al., 1987, Gene 53:63–71), on a pUC19 vector (Yannisch-Perron et al., 1985, Gene 33:103–119), prepared as described in WO 91/17243.

Bluescript SK- M.A. Alting-Mees and Short, J. M.,1989, Nucleic Acids Res. 17:9494–9494 pUC18 and pUC118: Viera and Messing, 1987, J. Meth. Enzymol. 153:3–11

EXAMPLE 1

Genomic Deletion of *Aspergillus oryzae* Alkaline Protease

The alp gene was deleted by a one step gene replacement method (G. May in *Applied Molecular Genetics of Filamentous Fungi*, 1992, pp. 1–25. J. R. Kinghorn and G. Turner, Eds.; Blackie Academic and Professional). The marker used was the *A. oryzae* pyrG gene; the *A. oryzae* strain used was a pyrG⁻ strain.

Cloning of the *Aspergillus oryzae* pyrG Gene

The *A. oryzae* pyrG gene was cloned by cross-hybridization with the *A. niger* pyrG gene (W. van Hartingsveldt et al., 1987, Mol. Gen. Genet. 206:71–75). A lambda library of partial SauI-IIA digested *A.oryzae* IFO 4177 DNA was probed at low stringency with a 1 kb DNA fragment from the *A. niger* pyrG gene. DNA from one positive clone was subcloned into a pUC118 vector. The resultant plasmid, pSO2, was shown to contain the pyrG gene by complementation with an *A. niger* pyrG mutant.

Construction of an *Aspergillus oryzae* pyrG Minus Strain

A pyrG deletion plasmid, pSO5, containing about 1 kb of pyrG flanking sequences on each end was constructed from the plasmid pSO2. *A. oryzae* IFO 4177 was transformed with this construct and transformants were selected by resistance to 5-fluoro-orotic acid, a phenotype characteristic of pyrG mutants. One transformant, HowB101, were shown by Southern analysis to have the expected deletion at the pyrG locus. Being a pyrG mutant, HowB101 requires uridine for growth. HowB101 can be transformed with the wild type pyrG gene by selection for ability to grow without uridine.

Figure 1:
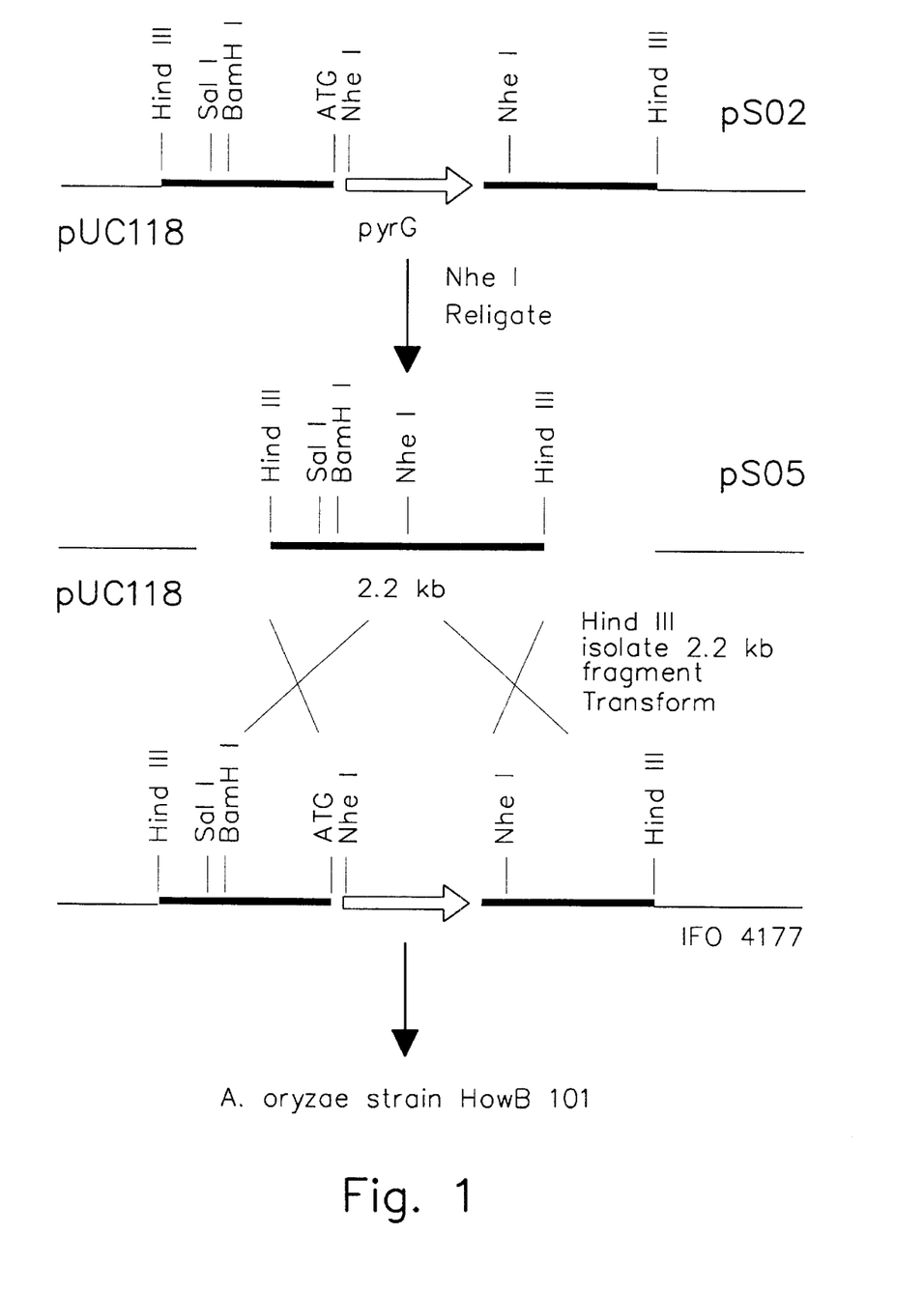
FIG. 1 shows the steps involved in the construction of HowB101.

The steps involved in the construction of HowB101 are illustrated in FIG. 1.

Construction of an *Aspergillus oryzae* alp Minus Strain

An *Aspergillus oryzae* alp⁻ strain was constructed by transforming *A. oryzae* strain HowB101 with the alp deletion plasmid pJaL212.

Construction of the Alkaline Protease Disruption Plasmid pJaL212

Figure 2:
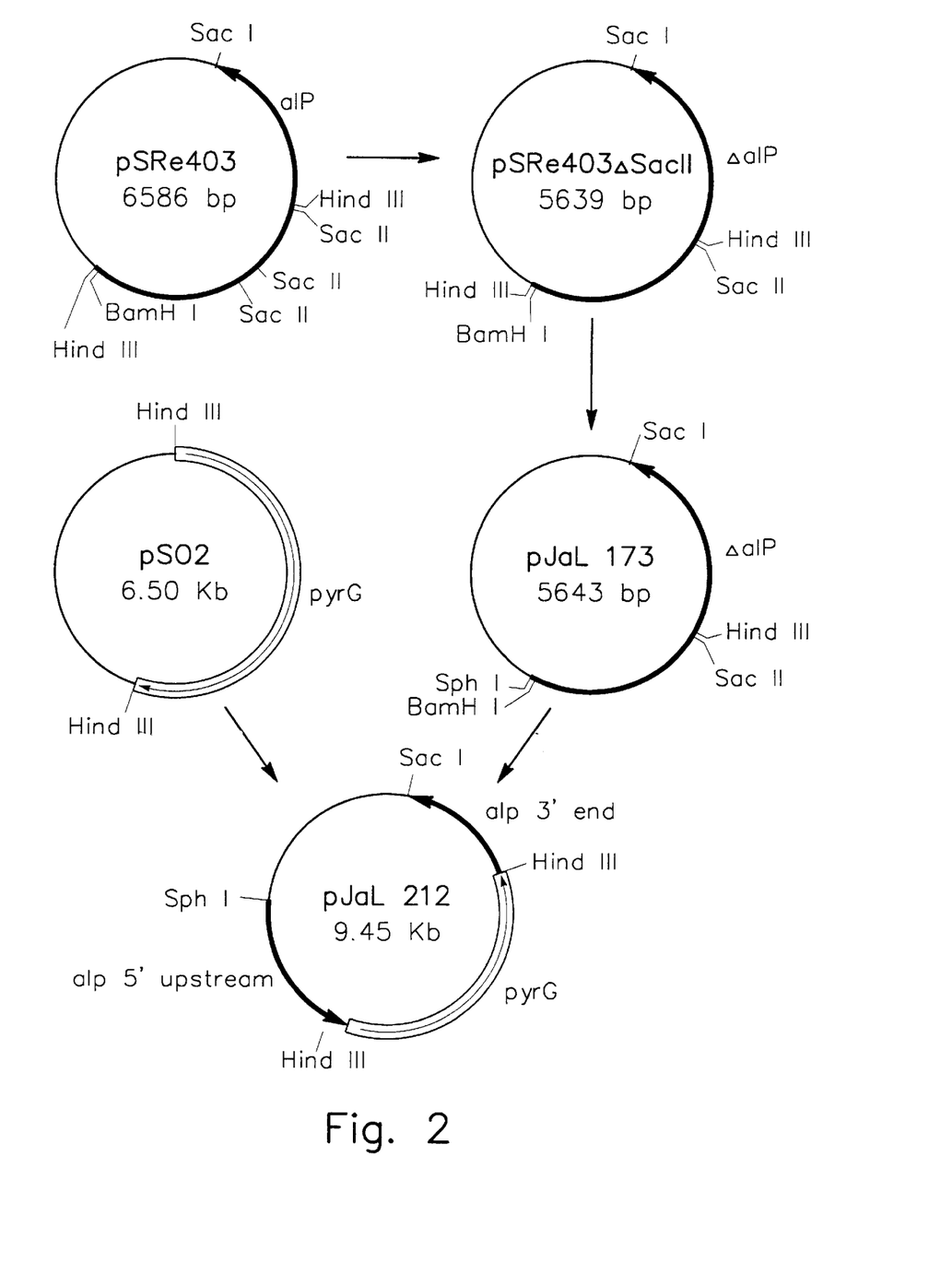
FIG. 2 shows the steps involved in the construction of pJaL212.

An *A.oryzae* IFO 4177 genomic library was established by partially digesting genomic DNA with Sau3A. Fragments were ligated into pUC19 digested with BamHI. The library was screened using degenerate oligonucleotides to known protein sequence fragments of the alkaline protease gene product. A plasmid containing a 3.9 kb Sau3A fragment was isolated in this way. This plasmid was named pSRe403.

pSRe403 was digested with SacII, and the 5.6 kb fragment was isolated and religated to form pSRe 403_SacII. This plasmid was partially digested with Hind III, the ends were filled in using Klenow polymerase and religated in order to remove the Hind III site in pUC19. The resulting plasmid was termed pJaL173. pJaL173 was digested with HindIII, and the 3.8 kb HindIII fragment, containing the pyrG gene of pSO2 was inserted into pJaL173 to form pJaL212. The construction of pJaL212 is outlined in FIG. 2.

Isolation of an *A. oryzae* alp Minus Strain

*A. oryzae* HowB101 was transformed with the 6.8 kb SacI-SphI fragment of pJaL212 using standard procedures. This fragment consists of 1.5 kb of the alp promoter, the pyrG gene and 1.5 kb of the 3' end of the alp gene. Transformants were selected by their ability to grow in the absence of uridine. After reisolation chromosomal DNA was prepared from 12 transformants, the DNA was cut with PstI and analysed by Southern analysis with a 599 bp PstI/SacII fragment from pJaL173 containing part of the alp gene as a radioactive labelled probe. Transformants which carry a deletion of the alp gene are easily recognized by the shift of wild type PstI band at 1.0 kb to a 1.9 kb band.

In four transformants the 1.0 kb PstI band shifted to the 1.9 kb band. One of these transformants was named JaL125.

Figure 3:
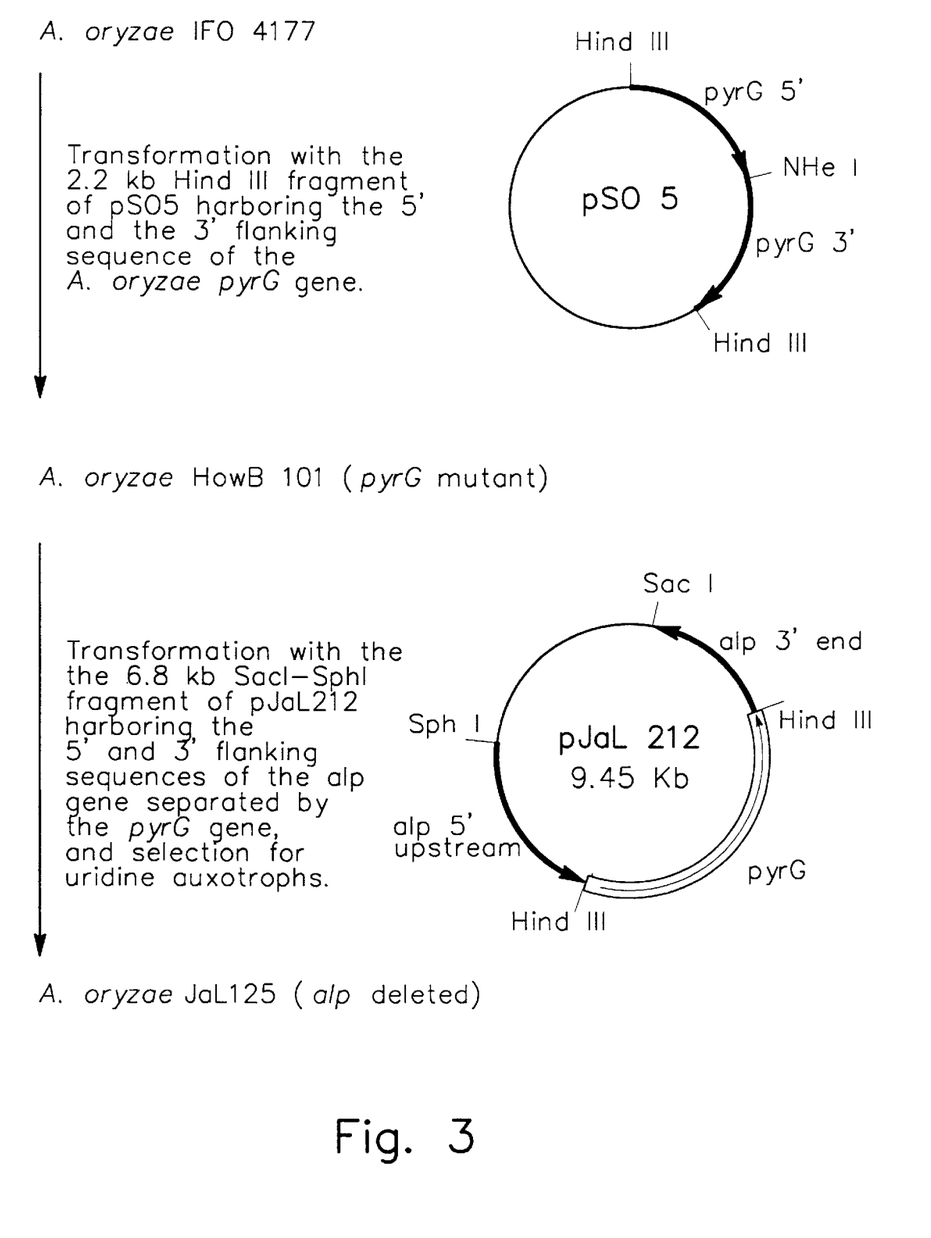
FIG. 3 show the steps involved in the construction of *A. oryzae* pJaL125 (alp deleted)

The steps involved in the construction of JaL125 are illustrated in FIG. 3.

EXAMPLE 2

Production of 45 kD Endoglucanase in *A. oryzae* Strain JaL125

Figure 4:
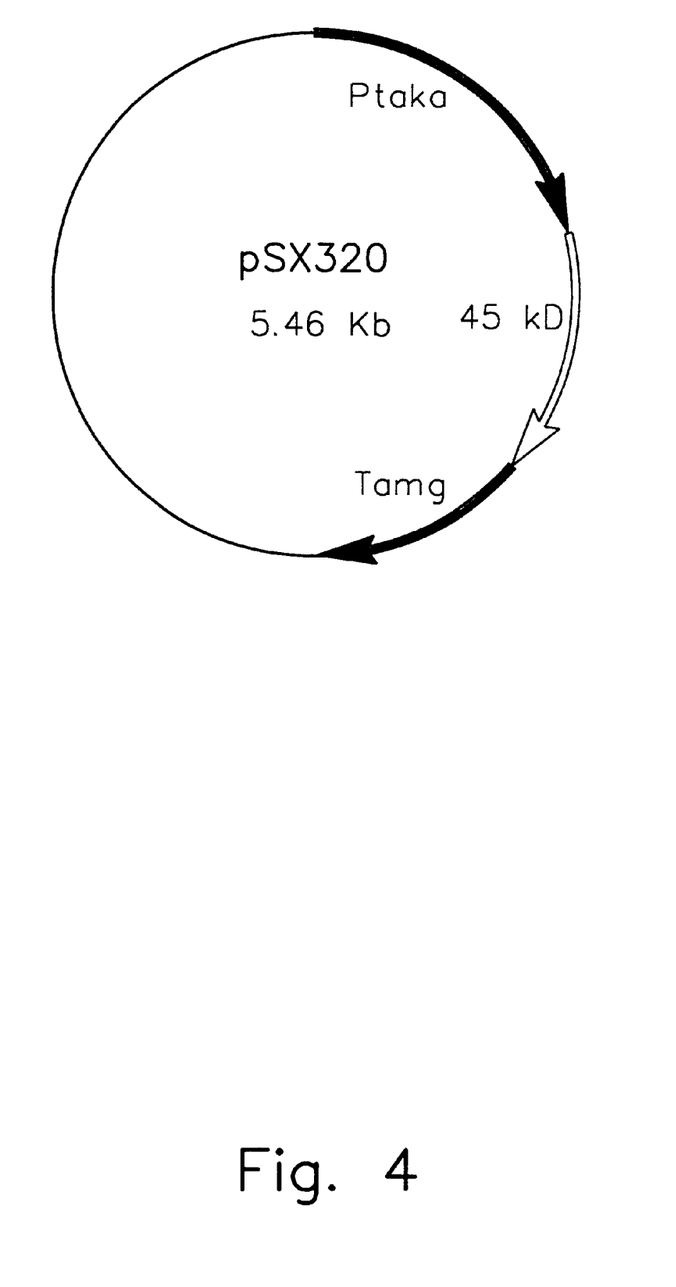
FIG. 4 shows pSX320.

*A. oryzae* strains IFO 4177 and JaL125 were transformed with the plasmid pSX320 (FIG. 4), which is a fungal expression plasmid for the 45 kD endoglucanase from *Humicola insolens*, by co-transformation with pToC90. Construction of the plasmid pSX320 has been previously described in EP 0 531 372.

Transformants were selected for growth on minimal medium containing 10 mM acetamide and screened for the presence of pSX320 by the ability to produce Carezyme®.

Figure 5:
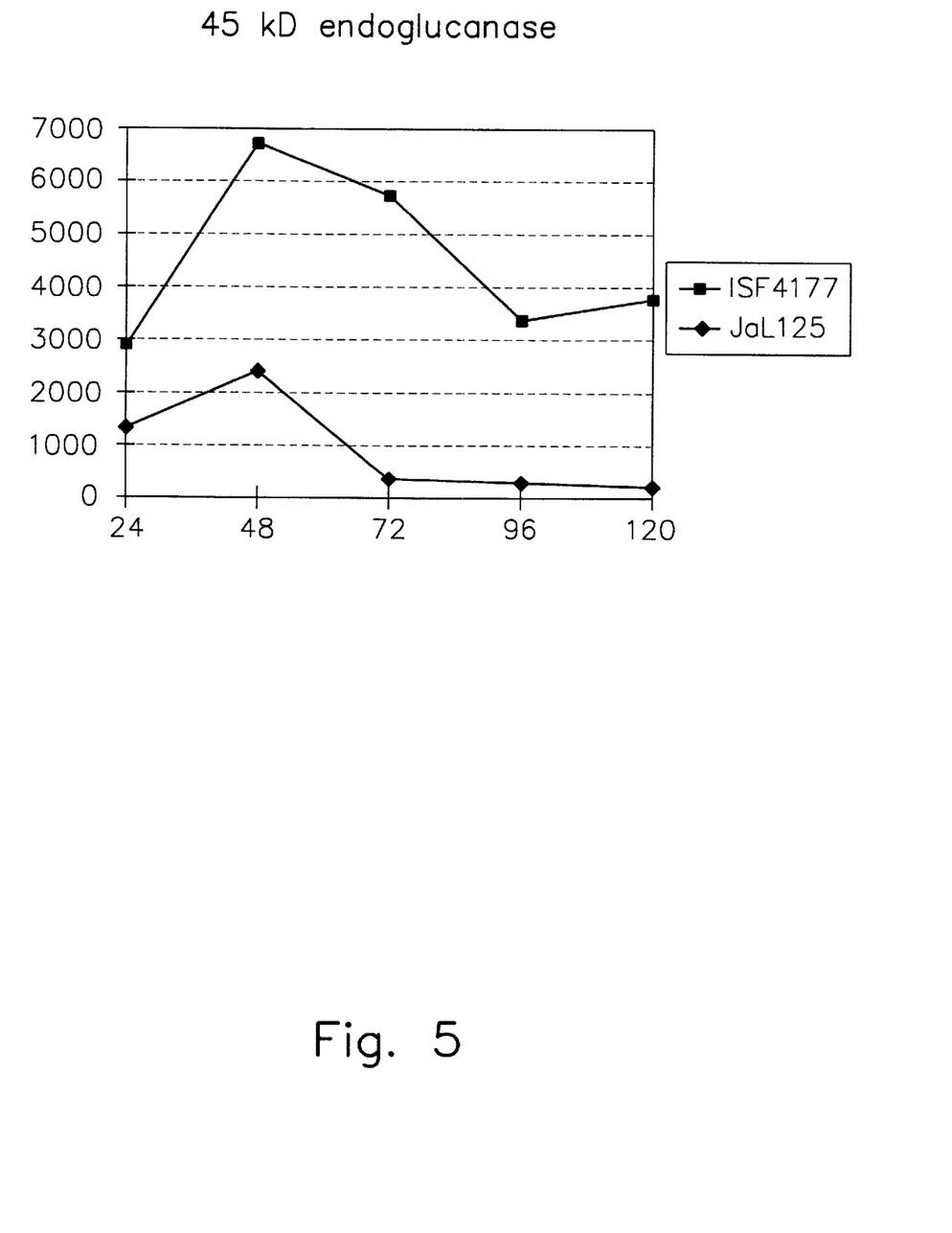
FIG. 5 shows the production of 45 kD endoglucanase in a host strain of the invention (*A. oryzae* JaL125) wherein alp has been deleted in comparison to a corresponding strain of *A. oryzae* in which alp has not been deleted.

One transformant from each strain was selected and grown at 30° C. in shake flasks containing 100 ml maltodextrin, soybean meal, and peptone for 5 days. Samples of the fermentation broth were taken every day and analysed by SDS-PAGE. The yield of the 45kD endoglucanase was quantified from the Coomassie Blue stained protein bands by use of the gel scanning system BioImage (BioImage System, UK). The results are shown in FIG. 5. The results indicate that more 45 kD endoglucanase is present in the fermentation broth of the strains in which the alp gene has been deleted than in the wild type strain which contains the alp gene. This indicates that the stability of the endoglucanase is enhanced by deleting the alp gene.

What is claimed is:

1. An *Aspergillus oryzae* cell, comprising a DNA sequence encoding a heterologous polypeptide and an alp gene encoding an alkaline protease, that is completely or partially inactivated, wherein the alp gene has a nucleic acid sequence that is at least 80% identical to SEQ ID NO:1.

2. The cell of claim 1, wherein the alp gene has a nucleic acid sequence that is at least 90% identical to SEQ ID NO:1.

3. The cell of claim 2, wherein the alp gene has a nucleic acid sequence that is at least 95% identical to SEQ ID NO:1.

4. The cell of claim 3, wherein the alp gene has a nucleic acid sequence that is at least 97% identical to SEQ ID NO:1.

5. The cell of claim 4, wherein the alp gene is SEQ ID NO:1.

6. A DNA construct comprising a modification of an alp gene that is at least 80% identical to SEQ ID NO:1 wherein said modification inactivates said alp gene.

7. A method for producing the cell of claim 1, comprising inactivating the alkaline protease gene by:
(a) cloning of the alkaline protease gene in question from a fungus of interest,
(b) producing a DNA construct comprising the alkaline protease gene, wherein a part of the gene, has been substituted, deleted, or extra DNA has been inserted within the gene,
(c) transforming said cell with the DNA constructs, and
(d) isolating transformants from which:
(i) no alkaline protease activity can be determined;
(ii) a reduced level of alkaline protease activity can be determined; or
(iii) alkaline protease(s) having lost its function can be obtained.

8. A method for producing the cell of claim 1, comprising inactivating the alkaline protease gene a process which comprises:

(a) construction of an expression plasmid resulting in the synthesis of an RNA molecule complementary to the mRNA transcribed from the alkaline protease gene;
(b) transformation of the host fungal cell with said expression plasmid and a suitable marker;
(c) selection of transformants using said marker; and
(d) screening selected transformants a reduction in the synthesis of the alkaline protease product in question.

9. A method for producing the cell of claim 1, comprising modifying the cell to produce lower levels of alkaline protease than the wild-type by a process comprising transforming a parent cell of said fungus with a DNA construct capable of causing reduced production of a functional alkaline protease when integrated into the genome of said fungus.

10. The method of claim 9, wherein said alkaline protease gene is an alp gene comprising the sequence of SEQ ID NO:1 or a DNA sequence having at least 80% identity thereof.

11. A method for producing a heterologous polypeptide comprising cultivating the cell of claim 1.

12. The method of claim 11, wherein said polypeptide is secreted into the extracellular medium by said fungal host cell.

13. The method of claim 12, further comprising recovering the polypeptide from said culture medium.

14. The method of claim 12, wherein the cell is cultivated at a pH in the range from 5 to 11.

15. The method of claim 14, wherein the cell is cultivated at a pH in the range from 6 to 10.5.

16. The method of claim 15, wherein the cell is cultivated at a pH in the range from 7 to 10.

17. The method of claim 16, wherein the cell is cultivated at a pH in the range from 8 to 9.5.

18. The method of claim 12, wherein the polypeptide is a glycosidase enzyme, cellulase, xylanase, alpha-galactosidase, polygalacturonase or cellulose 1,4-beta-cellobiosidase.

19. The method of claim 12, wherein the desired gene product is insulin, growth hormone, glucagon, somatostatin, interferon, PDGF, factor VII, factor VIII, urokinase, tPA, EPO, or TPO.

20. The method of claim 12, wherein the heterologous polypeptide is of fungal origin.

21. The method of claim 20, wherein the polypeptide is an amylolytic enzyme, beta-galactosidase, phytase, cellulytic enzyme, lipolytic enzyme, xylanolytic enzyme, proteolytic enzyme, oxidoreductase, pectinase, cutinase, or protein disulfide isomerase.

22. The method of claim 20, wherein the alp gene has a nucleic acid sequence that is at least 90% identical to SEQ ID NO:1.

23. The method of claim 22, wherein the alp gene has a nucleic acid sequence that is at least 95% identical to SEQ ID NO:1.

24. The method of claim 23, wherein the alp gene has a nucleic acid sequence that is at least 97% identical to SEQ ID NO:1.

25. The method of claim 24, wherein the alp gene is SEQ ID NO:1.

26. The method of claim 12, wherein the hetrologous polypeptide is of bacterial origin.

27. The method of claim 26, wherein the polypeptide is an amylolytic enzyme, beta-galactosidase, cellulytic enzyme, lipolytic enzyme, or proteolytic enzyme.

* * * * *

SEQUENCE LISTING

```
<160> NUMBER OF SEQ ID NOS: 1

<210> SEQ ID NO 1
<211> LENGTH: 3922
<212> TYPE: DNA
<213> ORGANISM: Aspergillus oryzae

<400> SEQUENCE: 1
ggatccataa tgagcacact tgaacctcgc atgagtgctc catatcttag atccatttga      60
gtcacgagcg tcgaagccaa ggctaaaaga aaagggacca agaccgccgc atatcggggt     120
ggctgaacaa tcgctgctag tgtgtacaca ggatacataa attaatcaag agccaatgac     180
gttatcgaag acatgatatt acttacttga tttgttgcgg tgctccgact caactggatt     240
cagatggaag ggaagggatt cttgatcagg ctcgtcccgg gatgaccatt gctcctctcg     300
aatcgagaca atgttgaatg cccaggatga cgattgagag cgagatatta aaaaagagat     360
taagggttga cgattgccaa cggaagcccg atggaagaag aaatgccaag aatttggctg     420
cctggatgtt agtgccgttt agcctcaggc cccagctgaa tccctgccaa tcacgaggca     480
gggctcacca cctccaaccc ttacacaaga ctcgccctcg ctctttcctg caggtcctct     540
```

-continued

```
gcttactttc cctcttttc cctcctgaaa tgccccgaga atgccgtccg gagcttagga    600
aagctacgac ggcttaatgt tctaatttcc cccaccgacc tgccctggcc agttagaccg    660
ccggacccat cgaatgcaac atcaccaaca ctaatttacc tgcatctctg tcagcccact    720
gggtttaact agatatgcca aggacttgct tggctggttt atgcatgaag agagatgggc    780
actagtgcgt gcgggaccac aaacctcacc tgcagagggc tcatgcacct gaaagactgc    840
caatgatcat ttgactggtt aggtcaaggg gttaggctta gagcccttg ctaatgccga    900 tgccgcctct ttgactgcca catttcttgg cttcccctct tggcccctcc cgtcccttga    960
tgccaagggc cttggtggct cggactcccg gcggtaggct ggccacctac tcatggcgtg   1020
cggagatggg ccattcaggt tgtgcctaat gacatactct gatgccgacg ggaaggccgg   1080
ctgcttgctg gtgtcattgg cttctcgaat gactcggagg attgtcgtct tgcaggactt   1140
ttgtgtaaca acaggggccg acagttggcg tggctgccgt ggatatgctt ttgctgcgag   1200
ccatggttat tctgcggaac gaaaccaccc tcccacccaa acagggctaa tgtgcccagg   1260
tcctgatacc atcagaagac ctccaggagc acatgcctgt tcgcataacc gtggtgtagc   1320
accaggaatt gcttagctta gcttcttcga ctgggggcc agaaagtgct tatcgcaaag   1380
atcccacttc tttgtgtgat agccctcc gcggcccttg atcaagccgt tctcgctcgc   1440
ccataccgaa accgcgatat tataggtgca gatggttatt attcttttc tttttctttt   1500 tctttgcttc tcatgcagcc ccatacgttg ccgaatttgg ctacacctg gggctcattc   1560 ttcgaagttt agattccgac aagacctcag cacccaatca aaaccttga ttcctgataa   1620 aagacgtgga aaaagcgga tatcgcgtga ggatgccaag caaagggaat gggtcacatt   1680
gatctctgtc gcgctgttag gatgatcttc actcctaaag gcatcgccgc ggcattaggc   1740
ccttccctgt ccaagatatc ggttactcct ctcattatgg cgagctactt tgtgaattaa   1800
ttgactgagg gatataccac cttcccttg aaggtaccga gccactacct tgagcgttag   1860 ttacttttc gaggaaagca tcctatgcta gtctctgcca atcactgcag cgtcgacaac   1920
ttgccatagc cttgtgttct tcacggtcta tcggaacacc cgttcatgac tgaaaggggt   1980
cagcgtccgt ggtggtcaac atcattctca tctttcatca tgcccgctga ttgatagagt   2040
aatttccggt ggagcacaac gccgtcctct gagatgcaat gtcaccctgt aagtttcaac   2100
tacaatctgt agtacagagc atccttgtac ttgcatgctg tgcaagtgat ccaaatccgt   2160
agaacttgct cgagaacagg gaaatataga actcctgaag gttataaata ccacatgcat   2220
ccctcgtcca tcctcacttc catcatcaag ccagcggttt ctatcctccg acttgagttg   2280
ttcttgcgca tctttacaat cttctcatca tgcagtccat caagcgtacc ttgctcctcc   2340
tcggagctat ccttcccgcg gtcctcggtg ccctgtgca ggaaacccgc cgggccgctg   2400
agaagcttcc tggaaagtac attgtcacat tcaagcccgg cattgacgag gcaaagattc   2460
aggagcatac cacctgggct accaacattc accagcgcag tctggagcgt cgtggcgcca   2520
ctggcggtga tcttcctgtc ggtattgagc gcaactacaa gatcaacaag ttcgccgcct   2580
atgcaggctc tttcgacgat gctaccattg aggagattcg caagaacgaa gatgtttgtg   2640
gtcatccgct cgcatttttg aatgacagct aactcgcgcc caggttgcct acgtcgagga   2700
ggaccagatc tactacctcg atggcctgac tacccagaag agtgcccct ggggtctggg   2760 cagcattcc cacaagggcc agcagagcac cgactacatc tacgacacta gtgccggcga   2820
gggcacctat gcctacgtgg tggatagcgg tgtcaatgtc gaccatgagg agttcgaggg   2880
```

-continued

| | | | | | |
|---|---|---|---|---|---|
| ccgcgccagc | aaggcctaca | acgctgccgg | tggtcagcat | gtggacagca | ttggccatgg | 2940 |
| cacccacgtt | tccggcacca | ttgctggcaa | gacttatggt | atcgccaaga | aggccagcat | 3000 |
| cctttcggtc | aaagtttcc | agggtgaatc | gagcagcact | tccgtcattc | ttgacggctt | 3060 |
| caactgggct | gccaacgaca | ttgttagcaa | gaagcgtacc | agcaaggctg | caatcaacat | 3120 |
| gagcttgggt | gagtttacat | tgttcttctc | tacttggaac | gcgcgagcgc | taatttcaaa | 3180 |
| aacacaggcg | gtggctactc | taaggctttc | aacgatgcgg | tcgagaacgc | attcgagcag | 3240 |
| ggtgttctct | cggttgtcgc | tgccggtaac | gagaacgtac | gtctcccctc | catcgcgcaa | 3300 |
| agacgaattc | gtaactgact | tgattttctt | agtctgatgc | cggccaaacc | agccctgcct | 3360 |
| ctgcccctga | tgccatcact | gttgccgcta | tccagaagag | caacaaccgc | gccagtttct | 3420 |
| ccaactttgg | caaggtcgtt | gacgtcttcg | ctcccggtca | agatatcctt | tctgcctgga | 3480 |
| ttggctcttc | ctctgccacc | aacaccatct | ctggtacctc | catggctact | ccccacattg | 3540 |
| tcggcctgtc | cctctacctc | gctgcccttg | agaacctcga | tggcccgct | gccgtgacca | 3600 |
| agcgcatcaa | ggagttggcc | accaaggacg | tcgtcaagga | tgttaagggc | agccctaacc | 3660 |
| tgcttgccta | caacggtaac | gcttaagtac | caggagtacg | tcgcaggatt | ctaccattgt | 3720 |
| tactggaata | caatgatgat | tagaaaacga | agagcgttat | gattcggacg | gatatatgca | 3780 |
| tggcacccat | acagcgtgat | acataggctg | tttgctcaag | aattaggatt | ttatctgaat | 3840 |
| ccatgtacag | agtatactta | tgttagtagt | caataaaatc | ttggctttct | aattttgtcc | 3900 |
| catctacaag | gggtcgtcga | tc | | | | 3922 |